United States Patent [19]

Nelson

[11] 4,239,089
[45] Dec. 16, 1980

[54] STETHOSCOPE CHESTPIECE

[75] Inventor: Frederick W. Nelson, Cottage Grove, Minn.

[73] Assignee: Minnesota Mining and Manufacturing Company, Saint Paul, Minn.

[21] Appl. No.: 65,146

[22] Filed: Aug. 9, 1979

[51] Int. Cl.³ .............................................. A61B 7/02
[52] U.S. Cl. .................................... 181/131; 181/137
[58] Field of Search ................. 181/131, 137; D24/20

[56] References Cited

U.S. PATENT DOCUMENTS

| 3,152,659 | 10/1964 | Littmann | 181/137 |
| 3,224,526 | 12/1965 | Weber | 181/137 |
| 3,515,239 | 6/1970 | Machlup et al. | 181/137 |

Primary Examiner—Michael L. Gellner
Assistant Examiner—Thomas H. Tarcza
Attorney, Agent, or Firm—Cruzan Alexander; Donald M. Sell; Carolyn A. Bates

[57] ABSTRACT

A two-microphone stethoscope chestpiece is dislcosed wherein the locking mechanism for securing the shaft within the body of the chestpiece against axial movement and the indexing mechanism for aligning the shaft with the selected microphone are combined into a single spring having a C-shaped portion and a leg extending axially from one end thereof. The spring is positioned partially within grooves in the shaft and partially within corresponding slots in chestpiece body. Upon rotation of the shaft, the leg portion of the spring clicks into one of two opposed slots in the chestpiece body and secures the shaft in proper alignment with the selected microphone.

5 Claims, 5 Drawing Figures

U.S. Patent            Dec. 16, 1980            4,239,089
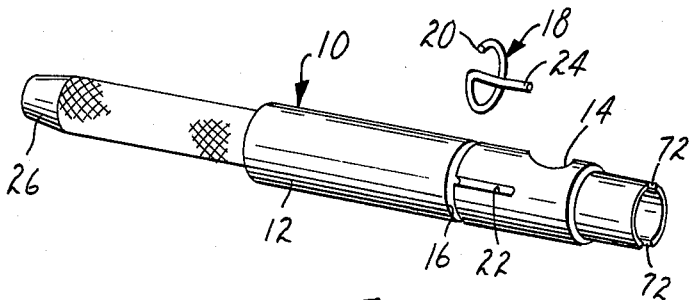
FIG. 1
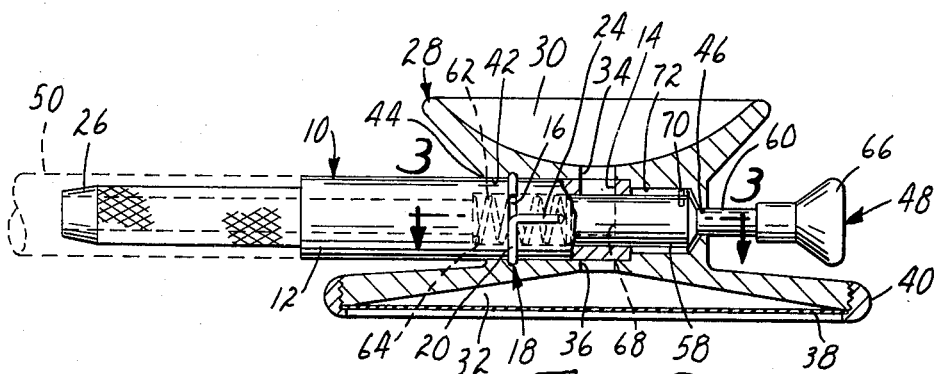
FIG. 2
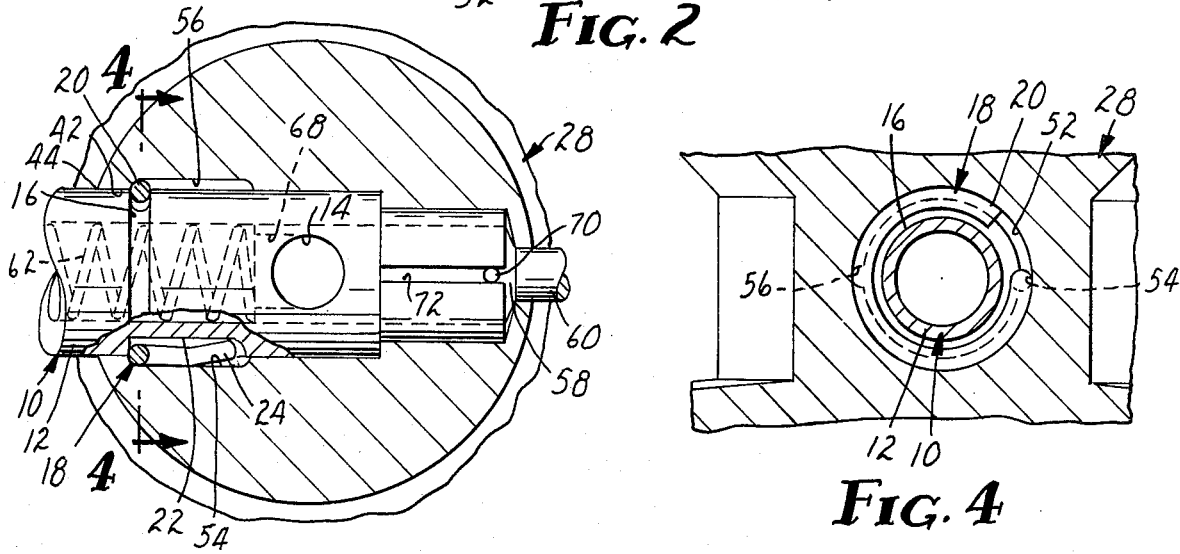
FIG. 3
FIG. 4
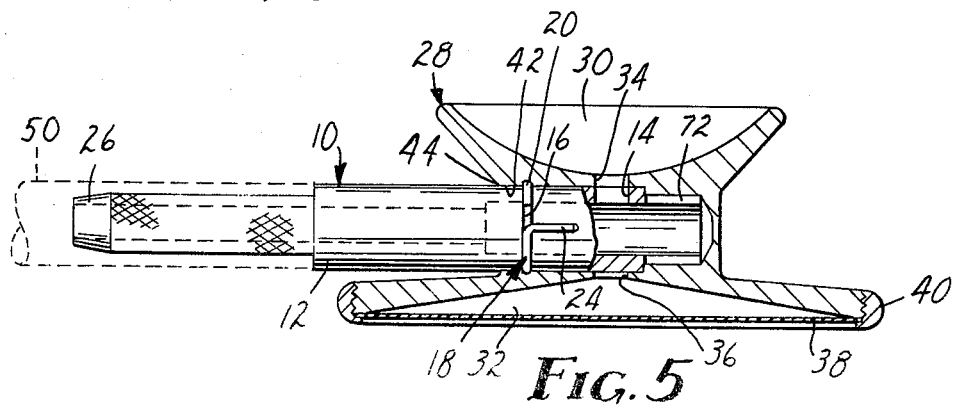
FIG. 5

STETHOSCOPE CHESTPIECE

The present invention relates to a two-microphone stethoscope chestpiece having novel and improved means for retaining the hollow stem in the body of the chestpiece and for selectively aligning one of the two microphones with the hollow stem.

Two-microphone stethoscope chestpiece constructions are well known in the art and generally have a hollow stem or shaft secured in a body member of the chestpiece for rotation into positions where an opening in the stem selectively connects an apex of one of the microphones e.g., "bell" or "diaphragm," with a sound tube engaged with the stem. Such stethoscope constructions frequently require relatively costly and complex means for mounting and rotation of the stem. Prior to the present invention, separate means were required to perform these two functions.

U.S. Pat. No. 3,152,659 discloses a two-microphone stethoscope chestpiece in which the stem is secured against axial movement by means of a retaining ring which lies partially within a groove in the outer wall of the stem and partially within a groove in the wall of the cylindrical recess. Indexing of the stem in one of two selected positions, i.e. where the opening in the stem is either aligned with the opening to the diaphragm microphone or is rotated 180° to align with the opening to the bell diaphragm, is accomplished by a U-shaped or index spring positioned at the lower end of the stem. An enlarged "bight" portion projects radially outwardly beyond the stem and is adapted to engage diametrically opposite grooves formed in the wall of the tubular recess. On rotation of the stem during indexing the spring is forced from the grooves under tension until the stem is rotated 180° at which point the spring reengages the grooves. A similar U-shaped indexing spring is disclosed in U.S. Pat. No. 3,515,239.

A stethoscope chestpiece having a lock ring for securing the stem within the chestpiece body similar to that disclosed above in U.S. Pat. No. 3,152,659 is disclosed in U.S. Pat. No. 3,224,526. This patent discloses a separate and different means for aligning the opening in the stem to the openings in the microphones comprising a coil spring which lies transversely of the stem wholly within the stem having a stop, e.g. a ball bearing, mounted on it. The ball bearing seals the hole between the stem and the microphone which is not in use. When pressure is applied to the stem to rotate it the ball bearing is biased against the spring inside the stem and rotates with the stem. When the proper alignment is reached, the compression on the spring is released and the ball bearing is forced against the opening to the microphone not in use and prevents air leakage.

Unlike the two-microphone chestpieces of the prior art which have separate means for securing the stem within the chestpiece and for aligning the stem opening with the microphone opening, the present invention combines these functions into a single element. The combined locking and indexing means of the present invention provides a chestpiece which is easy to assemble and has a significantly longer useful life than chestpieces of the prior art. Furthermore, the locking and indexing means of the present invention is especially useful in "differential" stethoscopes having two or more chestpieces. Differential stethoscopes are particularly useful in listening to sounds which are generated by organs which are reproduced on both sides of the body, such as the lungs. Using segmental auscultation techniques one can compare the sounds of the lung with those of the other. Since lung disease is generally patchy, rarely occuring uniformly in one lung, or especially across both lungs, one is able to detect such disease by noting differences in sound between one side and the other, for example by noting differences in pitch, amplitude and phase between the sounds. Alternatively, one can compare sounds in a patient being examined with sounds from a known standard, such as a natural or synthesized healthy sound. Similar considerations are applicable to listening to sounds in vessels (e.g. arteries) in different limbs, whereby differences in the sounds of the arrival of blood pulses can indicate the status of the blood supply to the area.

When using a differential stethoscope it is necessary to provide each chestpiece with means for momentarily interrupting sound from that chestpiece by closing the opening to the stem in order for the user to concentrate his attention on the sound coming from the other chestpiece. It is desirable to switch quickly back and forth between the chestpieces to compare the sounds coming from one with those from the other. Such means for interrupting sound from one chestpiece should be conveniently positioned for quick activation by the user. A convenient arrangement is a spring activated valve that slips within the stem of the chestpiece to close the sound pathway to the microphone which can be controlled by the action of the forefinger on an external extension of the valve. Such a valve mechanism is illustrated in FIGS. 2 and 3 of the attached drawings. The valve activator button is positioned at the tip of the stem for convenient manipulation with the forefinger. The tolerances in this area are very close and a conventional U-shaped indexing spring such as that described in U.S. Pat. Nos. 3,152,659 and 3,515,239 would interfere with proper placement of the valve. The improved combination indexing and locking spring of the present invention is ideally suited for use in the chestpieces of a differential stethoscope containing such a valve mechanism.

According to the present invention there is provided an improved stethoscope with a readily assembled chestpiece and ear tube mounting assembly. The chestpiece comprises: (1) a body member forming axially opposed diaphragm and bell microphones, the body member having a cylindrical recess interposed between the microphones; (2) means forming aligned openings from the apex of each of the microphones through the body member; (3) a tubular shaft rotatably secured within the cylindrical recess of the body member; (4) means forming an opening through the wall of the shaft adapted on rotation of the shaft to be aligned selectively with either of the two openings in the microphones; and (5) means for rotatably securing the shaft within the recess against axial movement and for selectively aligning the opening in the shaft with either of the openings in the microphones.

The rotatable shaft is secured in the cylindrical recess in the body member against axial movement by a locking spring which also has a leg to index the shaft in desired rotational positions with respect to the body member. The spring is formed of roll spring stock which is circular in cross section and has a C-shaped end portion with a leg extending axially from one end. The C-shaped portion is received in a first groove extending around the shaft and spaced from the opening therein. A second groove perpendicular to the first groove extends axially along the shaft and receives the leg portion of the spring. Both the first and second grooves in the shaft have a depth at least equal to the diameter of the spring. The body member has a circular slot in the wall forming the cylindrical recess which is preferably one-half the diameter of the spring to receive the C-shaped portion after the shaft and spring are inserted into the recess. The leg is received by one of two opposed slots of similar depths in the body. The slots are positioned so that engagement with the leg of the spring and either of the slots causes proper alignment between the opening in the shaft and the opening to either of the two microphones.

Preferably the leg has a slight bend or bow along its length to reduce the forces needed to rotate the shaft and drive the spring into the groove in the shaft, permitting the shaft and opening to be aligned with one of the slots in the body member.

DESCRIPTION OF THE DRAWINGS

Further understanding of the invention will be facilitated by reference to the accompanying drawings wherein.

FIG. 1 is a perspective view of the shaft of the chestpiece showing the retaining and indexing spring detached;

FIG. 2 is a longitudinal sectional view of the chestpiece containing a valve mechanism for interrupting sound from the chestpiece;

FIG. 3 is an enlarged view, partially in section, taken along line 3—3 of FIG. 2;

FIG. 4 is an enlarged sectional view taken along line 4—4 of FIG. 3; and

FIG. 5 is a longitudinal sectional view of a second embodiment of the chestpiece.

Referring to the drawing wherein like reference numerals designate like or corresponding elements and referring particularly to FIG. 1, shaft 10 comprises an elongated hollow cylinder 12 having an opening 14 therein which is located so as to align with one of the openings to the microphones when the shaft is inserted into the body of a chestpiece. A first groove 16 is formed around the circumference of the shaft and spaced from the opening 14 to receive the C-shaped portion 20 of a spring 18 formed of wire stock. A second groove 22 joins the first groove 16 and is perpendicular thereto. Second groove 22 extends axially from first groove 16 toward opening 14 and receives leg portion 24 of the spring 18. Alternatively, first groove 16 may be formed closer to opening 14 and second groove 22 may extend axially away from opening 14. Grooves 16 and 22 are substantially equal in depth and are at least deep enough to completely receive the spring, i.e. have a depth equal to the diameter of the spring 18. The spring 18 must be completely contained within the grooves to enable the shaft to be inserted into the body of the chestpiece. The leg portion 24 of spring 18 must fit completely within the groove 22 to enable rotation of the shaft inside the body of the chestpiece. Hollow cylinder 12 has a tapered end 26 which is adapted to receive a piece of flexible tubing which connects the chestpiece to the ear tubes of the stethoscope.

FIGS. 2 and 5 show the chestpieces in longitudinal section. The embodiment of FIG. 2 contains a valve mechanism which enables the wearer to close off sound from the chestpiece. This embodiment is especially adapted for use in a differential stethoscope. Both the chestpieces of FIGS. 2 and 5 comprise a body 28 having a pair of sound receiving chambers 30 and 32. Bell-shaped sound receiving chamber 30 has an aperture 34 extending axially through it in alignment with an aperture 36 formed in sound-receiving chamber 32. A diaphragm 38 formed of a thin, flexible, resilient member is stretched and secured over the sound-receiving chamber 32. This diaphragm 38 may be formed with integral rim 40 or, alternatively, a separate ring 40 may be formed with a lower lip adapted to engage and secure the diaphragm 38 against the concave surface of sound chamber 32.

Extending axially into the body 28 is a cavity or cylindrical recess 42 which is open at one end 44, and which terminates in the embodiment of FIG. 5 within the body 28 intermediate the sound-receiving chambers 30 and 32. In the embodiment of FIG. 2 the cylindrical recess has a second open end 46 which is closed by a valve mechanism 48 extending therethrough. This cavity 42 is in fluid communication with the apertures 34 and 36.

The rotating shaft 10 is secured within the cavity 42 and tapered end 26 thereof extends from the cylindrical recess so as to be readily interengaged with a flexible binaural tube 50. The sound tube preferably comprises a conventional Y-shaped sound tube having binaural ear pieces in accordance with known practice in the art. If especially high acoustic properties are required a sound tube such as that described in copending application Ser. No. 951,875 filed Oct. 16, 1978 is recommended. The shaft is secured within the cylindrical recess against axial movement while permitting rotational movement by means of the C-portion 20 of the spring 18. The C-portion 20 of the spring 18 is partially held within the groove 16 in the shaft and partially within the slot 52 in the wall of the cylindrical recess. The engagement of the C-portion of the spring 18 with grooves 16 and 52 is shown in greater detail in FIG. 4.

Proper alignment and locking of the rotatable cylindrical shaft 10 within the recess 42 so that the opening 14 in the shaft communicates with the selected opening 34 or 36 in the microphones is accomplished by means of the leg portion 24 of the spring 18. As the shaft is rotated the leg portion 24 is forced completely into the groove 22 in the shaft. When the shaft is rotated to achieve proper alignment of the opening 14 with the openings 34 or 36 to the selected microphone, tension on the leg 24 is released by one of two properly placed slots 54 and 56 cut into the wall of the cylindrical recess. The depth of slots 54 and 56 is about half the diameter of the spring 18 and the side walls thereof are preferably slanted to allow the spring to enter and depart with a snap or detent action. These slots can be formed in the recess by a broach.

The engagement of the leg portion 24 of the spring 18 with the slots 54 or 56 in the wall of the cylindrical recess is best illustrated in FIG. 3.

Valve mechanism 48 for interrupting communication between opening 14 and the microphone is illustrated in the embodiment of FIGS. 2 and 3 and comprises a cylinder 58 which fits into the bore of hollow shaft 10 and has a stem 60 extending through the open end 46 of the cylindrical recess 42 opposite the end 44 which receives the shaft 10. The cylinder 58 contacts one end of coil spring 62 contained within the shaft 10. The opposite end of coil spring 62 rests against shoulder 64 formed within the hollow shaft 10. The exterior portion of stem 60 is threaded (threads not shown) and a tip 66 adapted to be manipulated with the forefinger is screwed onto the threads. An opening 68 in the cylinder 58 is positioned to align with opening 14 in the shaft 10. Aligning pin 70 on the cylinder 58 is slideably positioned within slot 72 of shaft 10 to prevent rotational movement of cylinder 58 within the shaft and maintain opening 68 in alignment with opening 14 in the shaft.

The cylinder 58 and coil spring 62 are constructed such that pressure on the tip 66 compresses coil spring 62 and forces cylinder 58 into the shaft 10 and opening 68 is moved past opening 14 thereby closing off sound coming from the microphone. The valve is shown in the open position in FIGS. 2 and 3 and sound is freely transmitted from the selected microphone into the shaft which communicates with the head set of the stethoscope. When pressure is applied coil spring 62 compresses and cylinder 58 is forced into the shaft 10 and opening 14 is closed.

The operation of the stethoscope chestpiece of this invention is extremely simple. The shaft 10 can be rotated by hand from the position shown in FIG. 5 where the bell microphone 30 is connected to the sound tube in the shaft to a position where the bell microphone is closed off and the diaphragm microphone 32 is interconnected with the sound tube. The leg portion of the spring snaps into the selected slot 54 or 56 with a click sound. The shaft is thus locked in proper alignment until further pressure is applied to rotate the shaft.

While the preferred embodiment of this invention has been shown and described, it should be understood that variations thereof are possible. The present invention is to be limited only to the spirit and scope of the appended claims which follow.

What is claimed is:

1. In a stethoscope chestpiece comprising a body member forming axially opposed diaphragm and bell microphones, said body member having a cylindrical recess interposed between said microphones; means forming aligned openings from the apex of each of said microphones communicating with said recess; a tubular shaft rotatably secured within said cylindrical recess; means forming an opening through the wall of said shaft adapted on rotation of said shaft to be aligned selectively with either of said openings in said microphones; means for rotatably securing said shaft within said recess against axial movement; and means for selectively aligning said opening in said shaft with either of said openings in said microphones, the improvement wherein said means for rotatably securing said shaft within said recess against axial movement and said means for selectively aligning said opening in said shaft with the opening in a selected one of said microphones are combined in a single spring member comprising a C-shaped portion and a leg extending axially from one end of said C-shaped portion, said C-shaped portion being positioned within a first peripheral groove having a depth at least as deep as the diameter of the spring material forming said spring member, said first groove being spaced axially from said opening in said shaft and said leg being positioned within a second axial groove having a depth at least equal to the diameter of said spring material, said second groove joining said first groove; said C-shaped portion being biased partially within a circular slot in the wall of said cylindrical recess, said circular slot having a depth which is about one-half the diameter of said spring material; and said leg being received by one of two opposed axial slots in said cylindrical recess which slots are perpendicular to said circular slot whereby upon rotational movement of said shaft said leg is biased into one of said axial slots to retain said opening in said shaft in alignment with said opening in the selected microphone.

2. The stethoscope chestpiece according to claim 1 wherein said leg has a bend along its length to reduce the force needed to rotate said shaft and engage said leg with one of said two opposed axial slots.

3. The stethoscope chestpiece according to claim 1 wherein said second groove in said shaft extends axially toward said opening in said shaft.

4. The stethoscope chestpiece according to claim 1 further comprising means for interrupting communication between said shaft and said microphone.

5. The stethoscope chestpiece according to claim 4 wherein said means for interrupting communication comprises a cylinder positioned inside said shaft having an opening in the side wall thereof which aligns with said opening in said shaft when said cylinder is in its normal position and a stem extending through the open end of said cylindrical recess opposite the end receiving said shaft said cylinder being axially moveable within said shaft against a spring whereby pressure on said stem compresses said spring and forces said opening in said cylinder past said opening in said shaft thereby interrupting communication between said shaft and said microphone.

* * * * *